United States Patent [19]

Nishihata et al.

[11] Patent Number: 4,699,776

[45] Date of Patent: Oct. 13, 1987

[54] SUPPOSITORIES CONTAINING ANALGESICS, ANTIPYRETICS OR ANTI-INFLAMMATORY AGENTS

[75] Inventors: Toshiaki Nishihata; Akira Kamada, both of Osaka; Hisayo Wada, Tokushima, all of Japan

[73] Assignee: R. P. Scherer Corporation, Troy, Mich.

[21] Appl. No.: 750,423

[22] Filed: Jun. 28, 1985

[51] Int. Cl.$^4$ .............................................. A61U 9/00
[52] U.S. Cl. ..................................... 424/16; 514/965; 514/966
[58] Field of Search ................... 514/966, 965; 424/16

[56] References Cited

U.S. PATENT DOCUMENTS

| | | | |
|---|---|---|---|
| 1,970,396 | 8/1934 | Scherer | 18/21 |
| 2,288,327 | 6/1942 | Scherer | 18/21 |
| 2,318,718 | 5/1943 | Scherer | 18/21 |
| 4,406,896 | 9/1983 | Higuchi et al. | 424/232 |
| 4,464,363 | 8/1984 | Higuchi et al. | 424/232 |
| 4,612,310 | 9/1986 | Knecht | 514/222 |

OTHER PUBLICATIONS

Nishihata et al., Chem. Pharm. Bull., 26:3378–3383 (1978).
"Advances in Pharmaceutical Sciences", edited by Bean, Beckett and Corlass, vol. IV, Academic Press (1974).
Ch. 8, "Suppositories", by Joachim Anschel and Herbert A. Lieberman, Lachman and Lieberman, "Theory and Practive of Industrial Pharmacy", Lea and Febiger (1976).
"Rectal Administration of Drugs", Senior.

*Primary Examiner*—Stanley J. Friedman
*Attorney, Agent, or Firm*—Allegretti, Newitt, Witcoff & McAndrews, Ltd.

[57] ABSTRACT

A rectally administered unit dosage form comprising a therapeutically effective amount of an analgesic, an antipyretic or an anti-inflammatory agent capable of being absorbed into the bloodstream from a rectal compartment and an adjuvant, said adjuvant comprising lecithin present in said dosage form in a sufficient amount to be effective in enhancing and prolonging the absorption rate of said analgesic, antipyretic or anti-inflammatory agent from the rectal compartment into the bloodstream, in conjunction with a nontoxic, pharmaceutically acceptable carrier and the methods of using said unit dosage form.

4 Claims, 3 Drawing Figures

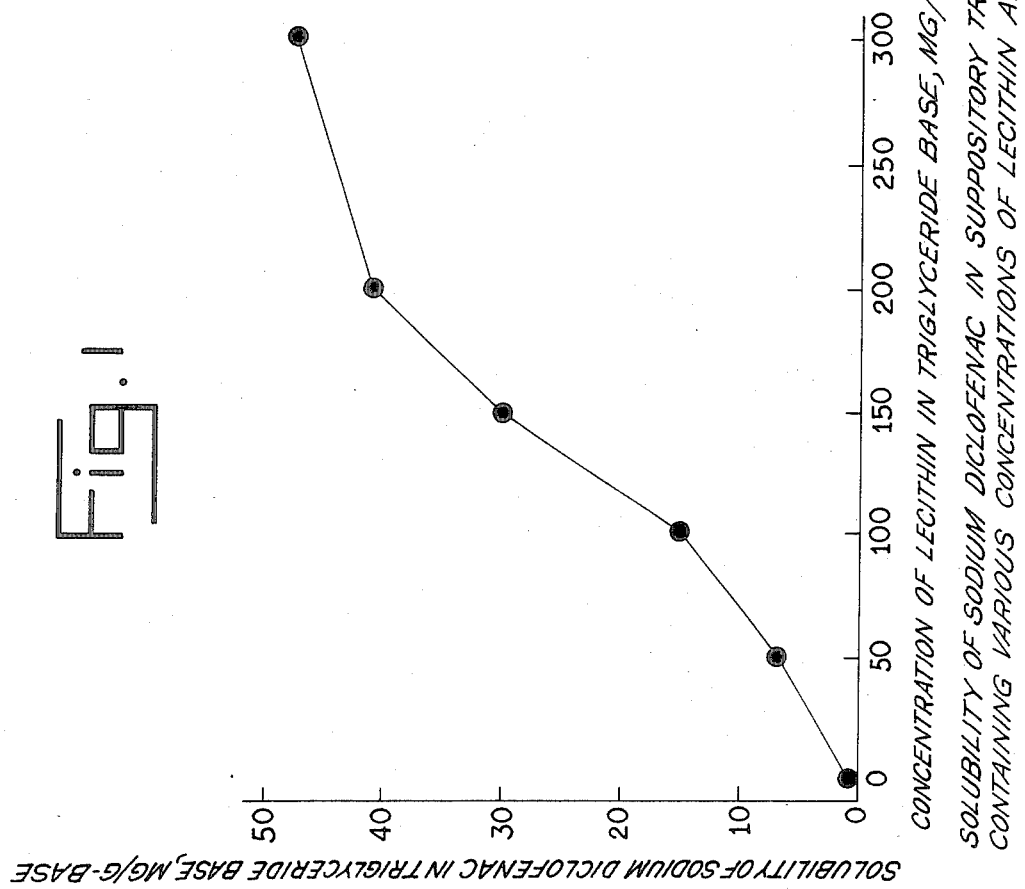

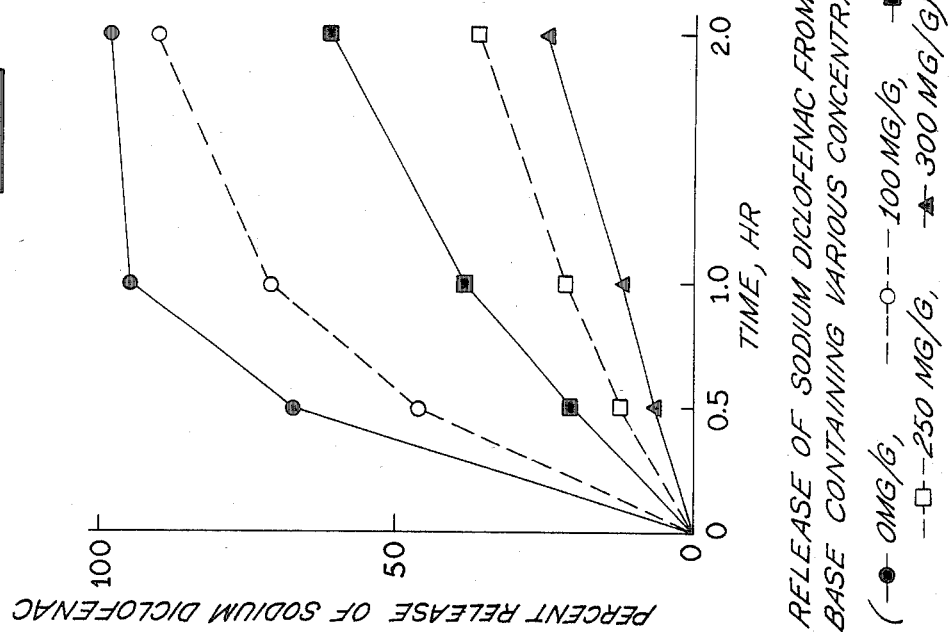

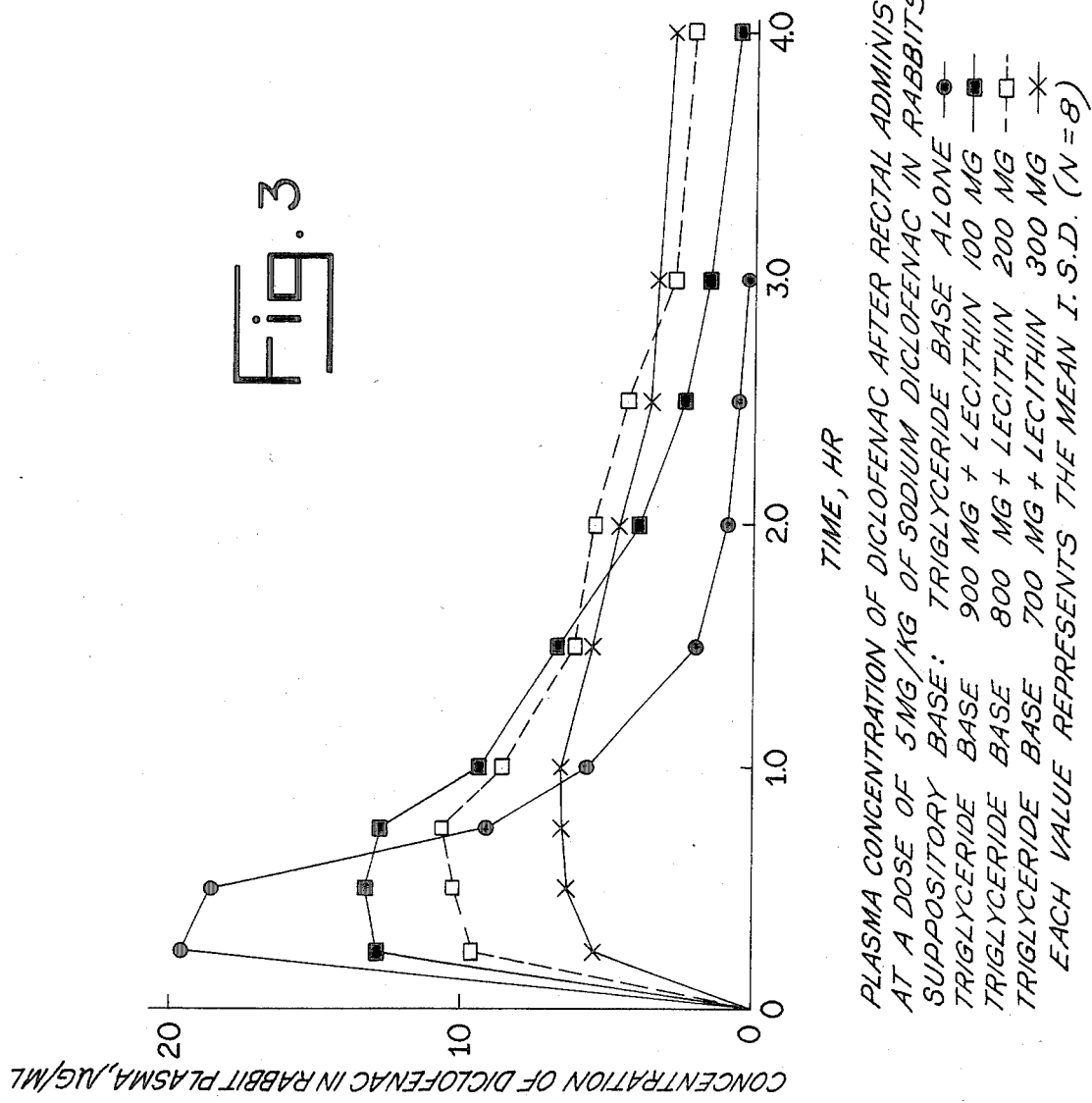

SUPPOSITORIES CONTAINING ANALGESICS, ANTIPYRETICS OR ANTI-INFLAMMATORY AGENTS

BACKGROUND OF THE INVENTION

1. Field of the Invention

This invention relates to a method for administering analgesics, antipyretics and anti-inflammatory agents by rectal delivery. It particularly relates to a method for enhancing and prolonging the rate of absorption of such rectally delivered medicinal agents from the rectal compartment to the bloodstream. This invention also relates to improved rectal suppository dosage forms used in the practice of such method.

2. Description of Related Art

One known method of drug administration is accomplished by the incorporation of a medically active substance in a "suppository," which, generally speaking, is a medicated solid unit dosage form typically intended for use in the rectum, vagina, and to a lesser extent, in the urethra. Rectal suppositories usually employ vehicles that melt or soften at body temperatures so that the drug may be released for use. Drugs administered in suppository form are administered for either local or systemic therapeutic effect. The action of the drug is dependent on the nature of the drug, its concentration, and its rate of absorption. Although rectal suppositories are commonly used for the treatment of constipation and hemorrhoids, that is, for local effect, such rectal suppositories are also administered rectally for systemic action. A wide variety of drugs may be rectally administered, as by the use of suppositories, including, for example, analgesics, antispasmodics, sedatives, tranquilizers, and antibacterial agents.

Rectal drug administration has many advantages over other routes of drug administration, such as oral administration and parenteral administration. For example, many drug substances that are given orally undergo inactivation in the stomach because of the acidic, enzymatic content of the stomach or the drug may be subject to digestive attack in the gut and/or to microbial degradation in the lower gut. Oral administration of drugs also directs all of the absorbed substances through the liver where they can be inactivated or reduced in effectiveness.

Rectal administration overcomes wholly, or in part, these known disadvantages of oral drug administration. Rectal drug administration also has advantages over parenteral administration. For example, rectal drug administration does not require highly trained personnel required for parenteral administration and also represents significantly less discomfort or hazard to the patient.

In view of the known disadvantages of oral and parenteral drug administration, drug administration by rectal delivery enables many drugs to be absorbed from the anorectal area, and yet retain their therapeutic value. The lower hemorrhoidal vein, surrounding the colon and rectum, enters the inferior vena cava and thereby bypasses the liver. Therefore, drugs are absorbed directly into the general circulation when rectally administered. For further background on rectal delivery of drugs, reference is made herein to an article entitled "Rectal Administration of Drugs" by N. Senior, "Advances in Pharmaceutical Sciences," edited by Bean, Beckett, and Corlass, Volume IV, Academic Press (1974) and to Chapter 8, "Suppositories", by Joachim Anschel and Herbert A. Lieberman, Lachman and Lieberman "Theory and Practice of Industrial Pharmacy", Lea and Febiger (1976).

Despite the known advantages of rectal administration of drugs, the rectal administration of drugs is not totally without problems. Many rectally administered drugs are poorly absorbed while others are slowly absorbed and, if so, are often inactivated or degraded while still in the rectal compartment. Generally, analgesics, antipyretics and anti-inflammatory agents which are rectally administered in the form of a suppository are rapidly absorbed with the result that the physiological effects only last for a short duration. Furthermore, the remarkably high blood levels in the early phase often cause undesirable side effects such as headache and vomiting. It would therefore be highly advantageous if rectally administered medicinal substances such as the analgesics, antipyretics and anti-inflammatory agents could have their rate of absorption from the rectal compartment to the bloodstream enhanced. Prolonging the rectal absorption of these drugs results in higher bioavailability and decreases or eliminates the side effects by suppressing the high blood levels in the early phase and sustaining the blood levels for longer duration.

SUMMARY OF THE INVENTION

It is therefore an important object of the present invention to provide a unique method for enhancing and prolonging the absorption rate of rectally administered analgesics, antipyretics and anti-inflammatory agents from the rectal compartment to the bloodstream.

It is also an object of the present invention to provide an improved rectal suppository unit dosage form which enhances and prolongs the absorption rate of rectally delivered analgesics, antipyretics and anti-inflammatory agents contained therein, the suppository preferably being formed using a soft triglyceride base.

It is a further important object of the present invention to provide an improved method for administering analgesics, antipyretics and anti-inflammatory agents by the use of rectal suppositories wherein enhanced and prolonged absorption results from the incorporation of lecithin into the unit dosage formulation.

It is yet another important object of this invention to provide an improved rectal suppository having an enhanced and prolonged absorption rate of analgesics, antipyretics and anti-inflammatory agents therefrom when in the rectal compartment, wherein lecithin is incorporated into a unit dosage formulation contained within a soft triglyceride base as a rectal suppository.

Further purposes and objects of this invention will appear as the specification proceeds.

The foregoing objects are accomplished by providing a method and suppository unit dosage form wherein the absorption rate of rectally administered analgesics, antipyretics and anti-inflammatory agents are enhanced and prolonged, the method comprising the steps of preparing a dosage form capable of being rectally administered, the dosage form comprising an effective unit dosage amount of the particular medicinal agent of a type which is capable of being absorbed from the rectal compartment into the bloodstream and lecithin, the lecithin being present in said dosage form in an amount sufficient to be effective in enhancing or prolonging the absorption rate of the medicinal agent into the bloodstream from the rectal compartment, and thereafter rectally administering the medicinal agent.

BRIEF DESCRIPTION OF THE DRAWINGS

Referring to the accompanying drawings, there is provided three graphs, to be hereinafter described in detail, illustrating the enhanced absorption rate of rectally administered drugs utilizing our improved rectal administration method and our improved rectal suppository dosage form wherein:

FIG. 1 is a graph illustrating the solubility of sodium diclofenac in a suppository triglyceride base containing various concentrations of lecithin at 40° C.;

FIG. 2 is a graph illustrating the release of sodium diclofenac from a suppository triglyceride base containing various concentrations of lecithin at 30° C.; and FIG. 3 is a graph illustrating the plasma concentration of diclofenac after rectal administration at a dose of 5 mg/kg of sodium diclofenac in rabbits using a suppository triglyceride base alone and containing various concentrations of lecithin.

DETAILED DESCRIPTION OF THE PREFERRED EMBODIMENTS

The present invention, generally, comprises the steps of preparing a dosage form capable of being rectally administered, wherein the dosage form comprises an effective unit dosage amount of an analgesic, antipyretic or anti-inflammatory agent capable of being absorbed into the bloodstream from the rectal compartment and an adjuvant, said adjuvant comprising lecithin present in the dosage form in a sufficient amount to be effective in enhancing and prolonging the absorption rate of the medicinal agent, and rectally administering the dosage form to the patient.

The method of this invention for enhancing the rate of absorption of analgesics, antipyretics and anti-inflammatory agents from the rectal compartment is useful for a wide range of medicinal agents which are capable of being absorbed into the bloodstream of a patient from the rectal compartment. The amount of the drug used in the method for enhancing its absorption typically varies over a wide range, but generally any therapeutically effective unit dosage amount of the selected drug may be used. Examples of analgesics, antipyretics and anti-inflammatory agents include, but are not limited to, indomethacin, sodium diclofenac, dipyrone and the like.

A specific adjuvant useful in the method and suppositories of the instant invention for enhancing rectal absorption is lecithin. It has been reported that the oil in water partition of a drug with low lipophilicity increases with the addition of lecithin to the lipid phase. T. Nishihata, et al., Chem. Pharm. Bull., 26: 3378–3383 (1978). It has now been found that lecithin can control the release rate of a drug from a triglyceride base thereby suppressing the high blood levels in the early phase and sustaining the blood levels for a longer duration.

The adjuvant lecithin is not considered novel per se and may be prepared by techniques known to those skilled in the art. As in the case of the medicinal agents used in the method and suppositories of the invention, the amount of the lecithin used may vary over a wide range. In general, the amount of the lecithin is selected in connection with the drug in order to be effective in enhancing and prolonging the absorption rate of the drug from the rectal compartment into the bloodstream.

The particular method for the rectal administration of the analgesics, antipyretics and anti-inflammatory agents is preferably by use of the appropriate size, shape or form of any of the various types of rectal suppositories known to the pharmaceutical art. Any nontoxic, pharmaceutically acceptable carrier may provide the base for the medicinal agent in conjunction with the lecithin. Useful rectal suppositories with which the present method may be used include, but are not limited to, cocoa butter suppositories, synethetic fat suppositories, hydrophilic suppositories, glyceryl gelatin suppositories, gelatin capsules including soft elastic gelatin capsule type suppositories, etc. A preferred form of suppository comprises a soft triglyceride base.

Another preferred form of suppository comprises a soft elastic gelatin capsule having an outer shell which encloses the medicinal agent and lecithin in a suitable vehicle which will not attack the walls of the seamless gelatin capsule. The shell encapsulates the active ingredient and incipients. The gelatin capsule shell may be formulated in accordance with conventional techniques for making filled, seamless, soft elastic gelatin capsules containing therapeutically effective unit dosage amounts of the active drug ingredient. For example, one conventional shell formulation includes about 30–53 parts by weight of gelatin, 15–48 parts by weight of a plasticizer, such as glycerin or sorbitol, and about 16–40 parts by weight of water. Additionally, the gelatin shell may contain preservatives such as mixed parabens, ordinarily methyl or propyl parabens, in about a 4:1 ratio. The parabens may be incorporated in the shell formulation in minor proportions as compared to the total weight of the shell formulation. Conventional gelatin capsules utilize gelatin having a bloom value of about 160–200 although this amount may be varied. Using conventional techniques, the gelatin composition is mixed and melted under vacuum conditions. The capsules may be simultaneously formed and filled using a conventional method and apparatus such as disclosed, for example, in U.S. Pat. Nos. 1,970,396; 2,288,327; and 2,318,718. The gelatin capsules are formed into a desired shape and size for insertion into the rectal compartment.

Likewise, in a conventional manner, any of the suppositories containing the medicinal agent may be prepared and formed into a desired shape and size for insertion into the rectal compartment. It is to be understood, however, that the particular method used for making the suppository of soft elastic gelatin shell is not considered part of the invention herein.

One of the more important uses of this method and suppository for rectal administration of analgesics, antipyretics and anti-inflammatory agents is in the administration of sustained release or programmed release dosage forms which will slowly release the medicinal agent into the rectal compartment. The present method and suppository permit the rapid clearance of the released drug into the bloodstream by way of the lower hemorrhoidal vein, instead of moving upwards into the lower gut. This technique thereby reduces or avoids loss of therapeutic effectiveness associated with passage of the drug through the liver.

More particularly, another important utility of the method of the present invention involves treating pyrexia, pain or inflammation in a mammal in need of such treatment which comprises rectally administering to the mammal the unit dosage form, as disclosed herein, containing an analgesic, an antipyretic and/or an anti-inflammatory agent as appropriate. The medicinal agent would, of course, be present in a therapeutically effective amount. Since the lecithin adjuvant promotes the rectal absorption of the drug, the amount of the drug in the dosage form for treating pyrexia, pain or inflammation will vary depending upon the amount of the lecithin used as well as the therapeutic effect desired.

Tests were conducted involving the present invention to illustrate the increased bioavailability of an analgesic, an antipyretic or an anti-inflammatory agent such as sodium diclofenac after rectal administration of suppositories containing sodium diclofenac and the lecithin adjuvant. The following data set forth specific experiments illustrating certain aspects of the present invention. These examples do not purport to be wholly definitive as to conditions and scope of this invention.

EXAMPLE 1

Referring to the accompanying graphs, the solubility of sodium diclofenac in a suppository triglyceride base containing various concentrations of lecithin at 40° C. is shown in FIG. 1. In this experiment, Witepsol$^R$H-15 (glycerol esters of mixtures of saturated vegetable fatty acids, predominantly lauric acid, derived from purified, specially selected coconut palm kernels, by separation into fatty acid and glyceride portions, fractional distillation of the fatty acid portion, followed by hydrogenation and esterification with glycerin, available from Dynamit-Nobel Chemicals, A.G., Troisdorf-Oberlar, Germany) is used as the base material. The suppositories containing lecithin are prepared as follows: Each level of lecithin (i.e., 50 mg, 100 mg, 150 mg, 200 mg, 250 mg and 300 mg per gram of suppository base) is added to the Witepsol$^R$H-15. Then, 25 mg per gram of suppository base of sodium diclofenac is mixed under fusion at 40° C. and solidified. The prepared samples are preserved in a refrigerator at 4° C. The solubility of sodium diclofenac in the triglyceride base containing each concentration of lecithin is determined at 40° C. The results in FIG. 1 show that the solubility of sodium diclofenac in the suppository base is increased in proportion to the lecithin concentration in the triglyceride base.

EXAMPLE 2

The release of sodium diclofenac from a suppository triglyceride base containing various concentrations of lecithin at 30° C. is shown in FIG. 2. Preparation of the various suppositories is carried out according to the procedure in Example 1. Release tests are conducted at 37° C. using Thomas' method. As the solubility of sodium diclofenac in the triglyceride base is low, the sodium diclofenac suspended in the suppository base is released quickly. The addition of lecithin delays the release of sodium diclofenac from the base. The results in FIG. 2 illustrate that when the lecithin content in a suppository is higher, the release of the sodium diclofenac from the triglyceride base is delayed.

EXAMPLE 3

The plasma concentration of diclofenac after rectal administration in rabbits at a dose of 5 mg/kg of sodium diclofenac in a suppository triglyceride base containing various concentrations of lecithin is shown in FIG. 3. Preparation of the various suppositories is carried out according to the procedure in Example 1. Absorption tests are performed using 8 albino male rabbits weighing approximately 2.8–3.1 kg. After the application of the suppository, the blood is taken from the aural vein with a time course, so as to separate the plasma and determine the plasmal diclofenac level with a high performance liquid chromatography. As the release of sodium diclofenac is delayed in the suppository containing lecithin (FIG. 2), the absorption is delayed and sustained. The results in FIG. 3 demonstrate that when the suppository used in the release test is applied to a rabbit, the suppository with higher lecithin content suppresses the remarkably high blood levels of diclofenac in the early phase and sustains the blood diclofenac levels.

While in the foregoing there has been provided a detailed description of particular embodiments of the present invention, it is to be understood that all equivalents obvious to those having skill in the art are to be included within the scope of the invention as claimed.

What is claimed is:

1. A rectally administered unit dosage form comprising a therapeutically effective amount of indomethacin, sodium diclofenac or dipyrone and an adjuvant, said adjuvant comprising lecithin present in said dosage form in a sufficient amount to be effective in enhancing and prolonging the absorption of indomethacin, sodium diclofenac or dipyrone from a rectal compartment into the bloodstream, said dosage form further comprising a nontoxic, pharmaceutically acceptable carrier.

2. The unit dosage form of claim 1 wherein said dosage form is a suppository.

3. The unit dosage form of claim 2 wherein said suppository comprises a soft elastic gelatin capsule containing indomethacin, sodium diclofenac or dipyrone and said adjuvant.

4. A method of enhancing and prolonging the rate of absorption of rectally administered indomethacin, sodium diclofenac or dipyrone from a rectal compartment into the bloodstream, said method comprising administering into said rectal compartment a rectal dosage form containing a therapeutically effective amount of indomethacin, sodium diclofenac or dipyrone and an adjuvant of lecithin, said adjuvant being present in said dosage form in a sufficient amount to be effective in enhancing and prolonging said absorption rate, in conjunction with a nontoxic, pharmaceutically acceptable carrier.

* * * * *